United States Patent [19]

Huthmacher et al.

[11] Patent Number: 5,041,655

[45] Date of Patent: Aug. 20, 1991

[54] METHOD OF PREPARING 1,6-DI(N$^3$-CYANO-N$^1$-GUANIDINO) HEXANE

[75] Inventors: Klaus Huthmacher, Gelnhausen; Axel Kleemann, Mühlheim; Horst Bethge, Hanau; Rolf Braun, Gründau, all of Fed. Rep. of Germany

[73] Assignee: Degussa Aktiengellschaft, Fed. Rep. of Germany

[21] Appl. No.: 241,116

[22] Filed: Sep. 6, 1988

[30] Foreign Application Priority Data

Sep. 4, 1987 [DE] Fed. Rep. of Germany ....... 3729530

[51] Int. Cl.$^5$ ............................................. C07C 277/02
[52] U.S. Cl. ................................... 564/106; 564/104; 564/303
[58] Field of Search ...................... 564/104, 106, 303

[56] References Cited

U.S. PATENT DOCUMENTS

| | | | |
|---|---|---|---|
| 2,686,203 | 8/1954 | Hechenbleikner | 564/106 |
| 3,428,576 | 2/1969 | Dickinson et al. | 564/104 X |
| 4,217,366 | 8/1980 | Kikumoto et al. | 564/353 X |
| 4,250,109 | 2/1981 | Uchikuga et al. | 564/104 |
| 4,537,746 | 8/1985 | Ogunbiyi et al. | 422/28 |
| 4,792,570 | 12/1988 | Nelson et al. | 564/353 X |

FOREIGN PATENT DOCUMENTS 63-208566  8/1988  Japan ................................... 564/104

Primary Examiner—Mary C. Lee
Attorney, Agent, or Firm—Cushman, Darby & Cushman

[57] ABSTRACT

An improved method of preparing 1,6-di(N$^3$-cyano-N$^1$-guanidino) hexane from alkali dicyanamide and a hexamethylene diammonium salt in alcoholic solution or suspension. The reaction is carried out in the presence of a limited amount of water and of a catalytic amount of a base, preferably a tertiary amine. The pH of the reaction mixture at the start of the reaction is 8 to 10. After the reaction is over, the reaction mixture is compounded with water at a temperature above 80° C. and the coarse product which crystallizes out is separated from the liquid phase.

Preferably, sodium dicyanamide and hexamethylene diamine dihydrochloride, preferably formed in situ from aqueous 1,6-diaminohexane and aqueous hydrochloric acid, are reacted at pH 9-9.5 in n-butanol in the presence of 0.1 to 20% by wt. water in relation to the solvent including water.

1,6-di(N$^3$-cyano-N$^1$-guanidino) hexane is obtained in a high yield (85-86%) and with great purity (95-97%) and with a considerably improved space-time yield.

16 Claims, No Drawings

METHOD OF PREPARING 1,6-DI(N³-CYANO-N¹-GUANIDINO) HEXANE

The invention relates to an improved method of preparing 1,6-di(N³-cyano-N¹-guanidino) hexane from an alkali dicyanamide and a hexamethylene diammonium salt. The method is simple to perform on an industrial scale and is distinguished in particular by shortened reaction times and increased space-time yields. In addition, a very pure product is obtained in a high yield.

BACKGROUND OF THE INVENTION 1,6-di(N³-cyano-N¹-guanidino) hexane, often designated as hexamethylene-bis-cyanoguanidine or hexamethylene-bisdicyandiamide, is a valuable intermediary product for the preparation of bisbiguanides and polybiguanides, which are used as disinfectants or pesticides (cf. e.g. British Patent 705,838 and Published European Patent Specifications EP 125,091; EP 125,092; EP 125,093; EP 126,567; EP 127,062).

One of the most important uses for 1,6-di(N³-cyano-N¹-guanidino) hexane is the manufacture of 1,6-di(N⁵-p-chlorophenyl-N¹-diguanido)-hexane, generally designated as chlorhexidine. Chlorhexidine is a very effective antibacterial and antiseptic agent against gram-positive and gramnegative bacteria.

Various methods have been described for preparing 1,6-di(N³-cyano-N¹-guanidino) hexane:

F. L. Rose and G. Swain (J. Chem. Soc., (1956) pp. 4422 -4425) react sodium dicyanamide and hexamethylene diamine dihydrochloride with each other in stoichiometric proportions in n-butanol by heating for 8 hours under reflux. The reaction proceeds according to the following equation:

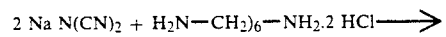

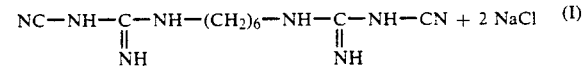

The raw product of the desired 1,6-di(N³-cyano-N¹-guanidino) hexane (I) which crystallizes out during cooling is filtered off together with sodium chloride which is formed and is present in an undissolved state. The product is subsequently washed with water and then dried. The yield of the product designated (I) should be 70 to 80 %. Nothing is said about the purity of (I); however, the indicated melting point of the product recrystallized from water (202°–203° C.) is still clearly under that of a pure product (209°–210° C.). Experiments performed by the applicant according to information in this document yielded contents of (I) of approximately 90 %. Therefore, the process suffers from the low product purity, which makes itself apparent in a reduced yield during the reaction to make chlorhexidine, and also in the moderate yield. In addition, the equipment expenses and the long reaction time required for this process result in a low space-time yield.

U.S. Pat. No. 4,537,746 describes an example of preparing 1,6-di(N³-cyano-N¹-guanidino) hexane (I) according to the method of Rose et al. and clearly refers to the document evaluated above.

The raw product (I) with a melting point of 200°–203° C. must be recrystallized in this case from a very large volume of a methanol-water mixture in order to obtain a product quality which is required for the subsequent reactions to produce disinfectants. The inventor has repeated this example. Instead of the 94 % yield described by this patent, only a yield of 45 % (63 % raw product) was obtained; moreover, the product purity after recrystallization was only 93.3 %. The example of U.S. Patent 4,537,746 provides no information on the quality of the sodium dicyanamide used - 1 mole corresponds to 89 g; however, 103 g were used.

J. Burns (J. Labelled Comp. Radiopharm. 19, 1982, pp. 1239–1250) discloses a method of preparing (I) in which the substances used in the previously cited methods are reacted with each other. Sodium dicyanamide is added in a slight excess in this process and the solvent is isopropanol dried with a molecular sieve. This method requires a 16-hour reaction time and produces (I) in a 57 % yield.

According to Published German Patent Specification DE-OS 29 32 951, 1,6-di(N³-cyano-N¹-guanidino) hexane can also be prepared by reacting hexamethylene diamine with an N-cyano-O (or S)-alkyl-iso (or isothio)-urea. The preparation of the urea starting material proceeds via the reaction of oxygen or thio-esters of N-cyanoimino carbonic acid with ammonia or an ammonium carbonate; the reaction with hexamethylene diamine takes place under pressure and requires a very long reaction time. Subsequently, the product must be purified with water and alcohol. Disadvantages of this and similar methods (cf. HU-PS 17,484 and 15,453) are the requirement for working under pressure, the very long reaction times, the formation of mercaptans when isothioureas are used, the use of expensive starting materials and the expense associated with the purification of the desired final product (I).

SUMMARY OF THE INVENTION

The object of the present invention is to provide an improved method for the preparation of 1,6-di(N³-cyano-N¹-guanidino) hexane from an alkali dicyanamide and a hexamethylene diammonium salt such as hexamethylene diamine dihydrochloride. A further object is to provide such a method which can be performed simply, reliably and very economically on an industrial scale. A still further object of the invention is to provide such a method which can make the product available in a high yield and with a degree of purity which makes possible a further reaction, e.g. to chlorhexidine, without recrystallization or other expensive purification.

It has been found, surprisingly and in contrast to previously known methods which carry out the reaction in an anhydrous alcohol, that the reaction can be accelerated by the presence of a limited amount of water and of a catalytic amount of a base and that a high yield is obtained if the pH at the start of the reaction is 8 to 10. It also has been found unexpectedly that the addition of water to the reaction mixture while it is still warm makes it possible to obtain a readily filterable reaction product with a higher degree of purity than was possible by means of the previously known methods which included expensive recrystallization.

Therefore, the objects of the present invention are achieved by means of a method of preparing 1,6-di(N³-cyano-N¹-guanidino) hexane by reacting an alkali dicyanamide with a hexamethylene diammonium salt in alcoholic solution or suspension while heating to at least 80° C., cooling the reaction mixture after the reaction is over, separating the crystallized reaction product, which was rendered essentially salt-free by treatment with water, and drying said reaction product. The method is characterized by carrying out the reaction in the presence of water and of a catalytic amount of a base. The amount of base is such that the reaction mixture, which contains the reactants in a stoichiometric proportion, has a pH of 8-10 at the start of the reaction, measured with a glass electrode at approximately 25° C. After the reaction is over, the reaction mixture is compounded with water at temperature above 80° C. and the crystallized reaction product is separated from the saline liquid phase.

The salts, alkali dicyanamide and hexamethylene diammonium salt contained in the reaction mixture at the start of the reaction, as well as the sodium salt produced, are present in the alcoholic solution primarily in suspended form. It is assumed that the salts are dissolved to a certain extent by means of the presence of water in accordance with the invention and/or are converted into a very fine suspension, which simplifies the reaction to the desired product. On the other hand, the fact that according to the invention the yield does not drop but rather is very high, in general around 85–95 % of theory, was surprising because water can hydrolyze the alkali dicyanamide. Therefore, 1,6-di($N^3$-cyano-$N^1$-guanidino) hexane cannot be obtained in water as a solvent by reacting e.g. sodium dicyanamide with hexamethylene diamine dihydrochloride. For the same reason, the amount of water used in the method of the invention is also limited, namely to 0.1 to 20 % by weight relative to the total amount of solvent (including water) present in the reaction mixture. The danger of hydrolysis increases as the amount of water in the reaction mixture and the temperature increase, for which reason at temperatures of about 100° C. or higher a water content of 0.5 to 5 % by wt., on the same reference base as above, is advantageous. However, too low a water content results in a slowing-down of the reaction and to a reduction of yield, obviously caused by the longer reaction time.

In accordance with a preferred embodiment of the invention, the reaction mixture is prepared in such a manner that an aqueous, optionally aqueous-alcoholic solution of hexamethylene diamine is compounded with aqueous hydrochloric acid, forming hexamethylene diamine dihydrochloride; the aqueous solution with a pH between 5 and 6 is then brought together, if not already present, with the alcohol, the alkali dicyanamide and the catalyst. The aqueous hexamethylene diamine dihydrochloride solution can be added directly to the alcoholic suspension of a alkali dicyanamide, in which instance the temperature of the suspension can be in the range from room temperature up to approximately 100° C. It is also possible to proceed in the reverse manner, that is, to place an aqueous-alcoholic, very fine suspension of hexamethylene diamine dihydrochloride formed in situ and with a milky appearance in a flask and to add alkali dicyanamide and to adjust the pH by the addition of the catalytically active base.

Whereas, in the embodiment previously described, water is added into the reaction mixture by means of the hydrochloric acid used and optionally by the hexamethylene diamine, which is commercially available at a reasonable price as 90 % aqueous solution, this can also take place entirely or partially by means of the alcoholic solvent used and/or the moisture of the added reactants or base and/or by means of a direct addition. The possibility of being able to add a moist, alcoholic solvent is a considerable advantage over the previously known methods because recovered solvent does not have to be dried before it is re-used.

The phrase "at the start of the reaction" denotes the point in time when the reaction mixture contains all components necessary for the reaction, regardless of whether the temperature of the mixture is at room temperature or at an elevated temperature.

After the reaction mixture has been prepared, it is heated to the desired reaction temperature in a range of approximately 80° C. to 170° C., preferably 110° C to 150° C., and held at approximately this temperature, usually with agitation, until the reaction is completed. The end of the reaction can be readily determined by a test using gas chromatographic methods of analysis.

It is advantageous, especially when a rather high concentration of water is present due to the preparation of the reaction mixture, that is, an amount of water in a range of approximately 5 to 20 % by wt. in relation to the solvent (including water) present, to lower the concentration of water to 5 to 0.5 % by wt. during the heating to the reaction temperature, by distilling the water off. This distillation can take place as an azeotrope with the alcohol and at normal pressure and/or reduced pressure. Insofar as, for example, an aqueous hexamethylene diamine dihydrochloride solution is added at a temperature around or above 80° C. into a suspension containing alkali dicyanamide, a part of the water can be distilled off as early as during the preparation of the reaction mixture.

At the start of the reaction, the reaction mixture containing the reactants in a stoichiometric proportion has a pH in a range of 8 to 10. The pH is measured in a customary manner, e.g. with a glass electrode. The range pH 8 to 10 is relative to a measuring temperature of approximately 25° C., which does not mean, however, that the reaction mixture must exhibit such a temperature at the start of the reaction. A pH outside the range pH 8 to 10 at the start of the reaction results in a diminution of the yield. A pH in a range of 9 to 9.5 at the start of the reaction is preferred because the product yield is generally the highest in this range.

The desired pH is adjusted by the presence of a catalytic amount of a base in the reaction mixture. The base can be added directly to the reaction mixture containing the other components in such an amount that a pH of 8 to 10 results at a measuring temperature of 25° C. Alternatively, the base can also be added entirely or in part with the alcoholic solvent used. In a preferred embodiment, e.g. when using n-butanol as solvent and triethylamine as base, a mixture of the moist, alcoholic solvent is distilled off together with the amine during and/or after the reaction and supplied as such to a subsequent batch. Insofar as the distillate forms two phases, aqueous and organic, the phases are separated from one another and the organic phase is supplied to the next batch.

Preferably, aliphatic or cycloaliphatic amines, N-heterocyclic bases or hexamethylene diamine are used for adjusting the pH. Preferred compounds of the named classes of compounds contain 5 to 7 carbon atoms and one or two nitrogen atoms such as e.g. triethylamine, N-methyl morpholine or pyridine.

The previously discussed features of the method of the invention result in an accelerated reaction of the alkali dicyanamide with the hexamethylene diammonium salt. The method of the invention, in contrast to the previously known methods based on the same reaction, makes it possible to reduce the reaction time; in preferred embodiments, it is possible to reduce the reaction time by more than half. Surprisingly, the yield is generally increased. The shortening of the reaction time and the associated raising of the space-time yield as well as the increase of yield make the method quite economical. This advantage is further increased in the embodiment which includes in-situ formation of hexamethylene diamine dihydrochloride from hexamethylene diamine and aqueous hydrochloric acid because it is no longer necessary to add the expensive salt directly. In addition, the alkali dicyanamide and the solvent can also be added in a moist state, which saves drying expenses.

Another feature which increases the economy of the method arises in the work-up after the reaction is completed. The filtration of the 1,6-di($N^3$-cyano-$N^1$-guanidino) hexane crystallized out of the alcoholic solvent, the washing out with water of the alkali salt which accumulated therein and the recrystallization were very time-consuming in the known methods and considerably limited the system capacity; at the same time, the reaction product was saline and/or contaminated in some other way. The invention solves these problems by compounding the reaction mixture with water after the end of the reaction, preferably after a part of the solvent has been distilled off, at a temperature above 80° C., cooling the mixture at the same time or subsequently and then separating the crystallized product from the saline, liquid phase. The salt formed dissolves completely in the liquid phase and the crystalline 1,6-di($N^3$-cyano-$N^1$-guanidino) hexane (I) accumulates in a pure, coarse, crystalline form which is therefore easy to filter. After the addition of sufficient water, the alcoholic solvent can be removed by distillation insofar as it forms an azeotrope with water or boils at a temperature below 100° C. at normal pressure. It is preferable to use alcohols which form an azeotrope with water and boil over 100° C. and separate them before the solid-liquid phase separation by azeotropic distillation. The product (I) contains practically no saline impurities and the residual moisture is very small if the phase separation is performed in customary solid-liquid separator devices such as filters or centrifuges. The product (I) thus is recovered in very pure form, generally over 95 %. An immediate further reaction can be performed without expensive purification such as recrystallization.

In a preferred embodiment the reaction mixture is compounded at a temperature above 80° C. with water after the reaction is completed, generally beginning at the last prevailing or only moderately lowered reaction temperature. After any removal of solvent, e.g. by azeotropic distillation, the mixture is cooled down to 25°–60° C., preferably 30°–50° C. The phase separation is subsequently performed at this temperature. Preferably, part of the solvent, often together with the base used, is removed by distillation before the addition of the water, optionally during the reaction itself. The amount of solvent which is still present at the start of the addition of water and the amount of water to be added can be determined by a person skilled in the art by means of preliminary tests. Insofar as the alcoholic solvent used is not removed from the liquid phase before the solid-liquid phase separation, it must be recovered following the latter from the phase which is aqueous-alcoholic in this instance, e.g. by means of salting out or extraction. The addition of water at a temperature above 80° C., preferably above 110° C., is essential for the formation of coarse crystals of the reaction product. The space-time yield for the phase separation can be multiplied because of the good and rapid filterability which was made possible by this procedure.

Sodium dicyanamide is preferred among the alkali dicyanamides. Sodium dicyanamide is commercially available. As already stated, moist sodium dicyanamide can also be used.

The hexamethylene diammonium salt used is preferably hexamethylene diamine dihydrochloride (1,6-diaminohexane dihydrochloride). Other salts of 1,6-diaminohexane can also be used, preferably salts with strong acids, one equivalent acid per amino group.

According to preferred embodiments, sodium dicyanamide is used with hexamethylene diamine dihydrochloride, preferably formed in situ from hexamethylene diamine and hydrochloric acid.

The alcoholic solution for the reaction contains one or more mono or divalent alcohols as solvent. Preferred alcohols are those which contain 1 to 6 carbon atoms, especially primary alcohols. The use of a monovalent, primary alcohol with 3 to 5 carbon atoms such as n-butanol is especially advantageous. Especially preferred alcohols boil in a range of approximately 100° C. to 160° C. In the case of alcohols which boil at temperatures below the desired reaction temperature, the reaction can be carried out at an elevated pressure, but this is more expensive. The alcohol used can also include other functional groups such as e.g. methoxy to the extent they are stable under the reaction conditions. The alcoholic solution contains essentially alcohols and, generally, 0.1 to 20 % by wt. water in relation to solvent and water as solvent; however, other organic solvents which do not adversely affect the reaction can also be present. The reaction can also be carried out in aprotic solvents such as dimethyl formamide or sulfolane; however, the workup is more expensive.

The solvent recovered by distillation in the course of the reaction and/or during or after the addition of water is re-used in subsequent batches. If necessary, the solvent can also be recovered from the saline, aqueous phase; however, this is usually more expensive.

The 1,6-di(N3-cyano-$N^1$-guanidino) hexane prepared in accordance with the invention is dried in a customary manner, preferably at 70°–90° C. in a vacuum, e.g. in a fluid bed.

DETAILED DESCRIPTION OF PREFERRED EMBODIMENTS

The invention is illustrated by the following examples:

EXAMPLE 1 (REFERENCE EXAMPLE)

According to Example 1 of U.S. Pat. No. 4,537,746, 94.5 g (0.5 mole) 1,6-hexamethylene diamine dihydrochloride and 103 g of sodium dicyanamide with a content of 98 % (1.13 mole) are suspended in 700 ml n-butanol. The mixture is boiled for 8.5 hours under reflux. After the mixture has cooled off, the solid matter is filtered off and washed with ice water. The product is recrystallized from aqueous methanol (1.5 liters methanol and 2.5 liters water) and dried. 55.8 g, corresponding to 44.6 % of theory (in relation to hexamethylene diamine dihydrochloride), 1,6-di($N^3$-cyano-$N^1$-guanidino) hexane are obtained with a purity of 93.5 % (HPLC analysis).

The process was repeated; however, 90.8 g (1.0 mole) sodium dicyanamide (98 %) were added under conditions which were otherwise the same. Instead of recrystallization, the raw product was thoroughly agitated in 500 ml ethanol/water =1:1 at 45° C. and filtered off. The yield was 79.6 g (63.7 % of theory), the purity 94 %.

EXAMPLE 2 (REFERENCE EXAMPLE)

Diaminohexane dihydrochloride and sodium dicyanamide are added in an exact stoichiometric proportion and reacted in a manner which was analogous with the method of Example 1:

| 1,6-diaminohexane dihydrochloride | 23.6 kg (125 moles) |
| sodium dicyanamide (98%) | 22.7 kg (250 moles) |
| n-butanol | 175 l |
| reaction time | 8 hours |
| reaction temperature | 115-120° C. |

After the reaction is over, the mixture is cooled and centrifuged, then washed with cold water (approximately 100 liters) and recentrifuged. Since the product accumulates in a very fine granular form, the centrifugation requires several hours.

After drying, 24.9 kg 1,6-di($N^3$-cyano-$N^1$-guanidino) hexane are obtained, corresponding to a yield of 79.7 % of theory with a melting point of 200°-202° C. and a purity of 92 % (HPLC analysis); grain size: 50-100 μm (main portion)/scanning electron microscope.

EXAMPLE 3

71.7 g (0.556 mole) 1,6-diaminohexane (90 % aqueous solution) are added to 900 ml n-butanol; concentrated hydrochloric acid (approximately 90 ml) is added with agitation until the pH is approximately 6. Then, 105 g (2× 0.556 mole) sodium dicyanamide (94 %, residual moisture 6 %) is added and 5 ml triethylamine are added under pH measuring (glass electrode) at approximately 25° C. at which time a pH of 9.2 is set. This reaction mixture is heated and after it reaches approximately 97° C., about 600 ml of a butanol-water mixture are distilled off. After further heating, the mixture is heated for 3 hours under reflux (113°-115° C.) - the reaction mixture contains 2-4 % by wt. water in relation to the solvent including water present. Then, a part of the butanol is distilled off and 350 ml water is slowly added as early as during the boiling at which time the mixture cools off, a butanol-water azeotrope mixture distills off and the desired reaction product develops in the form of coarse, readily filterable particles. After having cooled off to 40°-50° C., the precipitate is removed by suction and dried in a vacuum at 90° C. 120 g (=86.3 % of theory) 1,6-di($N^3$-cyano-$N^1$-guanidino) hexane are obtained with a melting point of 208°-210° C. and a purity of 96.3 % determined by HPLC analysis.

EXAMPLE 4

Example 3 is repeated, but pyridine (approximately 10 ml) is added as a catalytically active base and the pH is set at 9.

119 g ( =85.6 % of theory) 1,6-di($N^3$-cyano-$N^1$-guanidino) hexane are obtained with a melting point of 207°-210° C. and a purity of 95.4 %.

EXAMPLE 5

105 g (1.112 mole) sodium dicyanamide (94 % / 6% residual moisture) in 900 ml n-butanol is placed in a 2-liter three-neck flask with an agitator, thermometer and distillation head, combined with 5 ml triethylamine and then heated to 80° C. An aqueous solution with a pH of 5.5 obtained from 64.5 g (0.556 mole) 1,6-diaminohexane (100 %) and 90 ml hydrochloric acid is added thereto. During further heating, 600 ml butanol-water mixture is distilled off and boiled for 3 hours under reflux, finally at 117°-118° C. The addition of water (350 ml) during the boiling and further work-up are performed in the manner described for Example 3. 119 g ( =85.6 % of theory) 1,6-di($N^3$-cyano-$N^1$-guanidino) hexane are obtained with a melting point of 208°-209° C., HPLC purity 95.9 %.

EXAMPLE 6

320 kg of a 90 % by wt. aqueous solution of 1,6diaminohexane (2.48 kmoles) with approximately 400 liters of hydrochloric acid (2×2.48 kmole) are adjusted to pH 5.5 in a 1.2 m³ agitated tank. 190 liters of water are distilled off under normal pressure.

4500 liters of n-butanol, 25 kg triethylamine and 465 kg sodium dicyanamide (95 %, 2×2.48 kmole) are placed in a 6 m3 agitated tank. The solution of hexamethylene diamine dihydrochloride prepared above is pumped into this mixture. Approximately 2000 liters of butanol-water mixture is drawn off during heating to the reaction temperature under reduced pressure. During the further reaction under reflux (113°-117° C.), 1000 liters of n-butanol are again distilled off under normal pressure. 3000 liters of water are slowly added as early as during the boiling, at which time any butanol still present distills off as azeotrope with water. After the mixture has cooled off to 40°-50° C., the solid matter present is centrifuged off.

The product can be filtered in a short time without difficulty.

550 kg ( =88.7 % of theory) 1,6-di($N^3$-cyano-$N^1$-guanidino) hexane are obtained; melting point 207°-209° C.; purity (HPLC) 96.4 %.

Grain size: 100-250 μm (agglomerates) / scanning electron microscope.

EXAMPLE 7

Example 6 is repeated. The same amounts are added and, during the heating under reduced pressure, 2000 liters of butanol-water mixture are distilled off and subsequently, within approximately 2.5 hours, another 2000 liters of butanol are distilled off under normal pressure. The remaining reaction mixture is compounded with 3000 liters of water, and residual butanol is drawn off up to an overhead temperature of approximately 100 . After the mixture has cooled off to 40°-50° C., it is centrifuged and the solid matter dried at 90° C. in a vacuum.

590 kg, corresponding to 95 % of theory, 1,6-di($N^3$-cyano-$N^1$-guanidino) hexane are obtained; melting point 208°-210° C., purity (HPLC analysis) 95.8 %.

Grain size: 100-250 μm (agglomerates) / scanning electron microscope.

EXAMPLE 8

Example 7 is repeated, but butanol redistilled from Example 7 is added. Triethylamine does not have to be supplemented because it distills off with the n-butanol and is therefore contained in the latter. The product is obtained in a 93.5 % yield; purity 95.3 %; melting point 207°-210° C.

What is claimed is:

1. A method of preparing 1,6-di($N^3$-cyano-$N^1$-guanidino) hexane by reacting an alkali dicyanamide with a hexamethylene diammonium salt in alcoholic solution or suspension while heating to at least 80° C., cooling the reaction mixture after the reaction is over, separating the crystallized reaction product, which was rendered essentially salt-free by treatment with water, and drying said reaction product, said reaction being carried out in the presence of 0.1 to 20% by weight water in relation to the solvent (including water) present in the reaction mixture, and of a catalytic amount of a base, wherein said catalytic base is selected from the group consisting of aliphatic or cycloaliphatic tertiary amines, N-heterocyclic amines, and hexamethylene diamines, and the amount of base being such that the reaction mixture exhibits a pH of 8-10 at the start of the reaction, measured with a glass electrode at approximately 25° C., the reaction mixture being compounded with water, at a temperature above 80° C., after the reaction is over, and the crystallized reaction product being separated from the resulting saline liquid phase.

2. A method as set forth in claim 1 in which the alkali dicyanamide is sodium dicyanamide.

3. A method as set forth in claim 1 in which the hexamethylene diammonium salt is hexamethylene diamine dihydrochloride.

4. A method as set forth in claim 3 including the step of forming an aqueous or aqueous-alcoholic solution of hexamethylene diamine dihydrochloride from hexamethylene diamine and a member of the group consisting of aqueous hydrochloric acid and a solution of hydrochloric acid in a mixture of water and alcohol.

5. A method as set forth in claim 1 in which the reaction mixture contains one or more mono or divalent alcohols which contain 1 to 6 carbon atoms.

6. A method as set forth in claim 5 in which the reaction mixture contains one or more primary, monovalent alcohols which contain 3 to 5 carbon atoms.

7. A method as set forth in claim 6 in which the alcohol is n-butanol.

8. A method as set forth in claim 1 in which the amount of water is 0.5 to 5 % by wt. and the reaction temperature is above approximately 100° C.

9. A method as set forth in claim 8 in which the reaction mixture initially has a water content of 5 to 20 % by wt. in relation to solvent (including water) present and, at the start of the reaction, the water content is lowered by distilling off water until the water content is 0.1 to 5 % by wt. in relation to solvent (including water) present.

10. A method as set forth in claim 9 in which the water is distilled as an azeotrope with the alcohol.

11. A method as set forth in claim 1 in which the pH of the reaction mixture is set at the start of the reaction to a value of 9 to 9.5, measured with a glass electrode at approximately 25° C.

12. A method as set forth in claim 1 in which the reaction is carried out by heating to 80° C. to 170° C.

13. A method as set forth in claim 12 in which the reaction is carried out by heating to 110° C. to 150° C.

14. A method as set forth in claim 1 in which, after the reaction is over, the reaction mixture is combined with water at a temperature above 80° C, any solvent still present is distilled off, the mixture is cooled to approximately 25° C. to 60° C. and the crystalline phase is separated from the liquid phase at this temperature preferably after a part of the alcoholic solvent has been removed by distilling it off.

15. A method as set forth in claim 14 in which the mixture is cooled to 30° C. to 50° C.

16. A method as set forth in claim 1 in which the reaction is carried out essentially at 112 to 120° C., triethylamine is used as catalyst, a part of the n-butanol is distilled off after the reaction is over and, after the addition of water, any n-butanol still present is distilled off as an azeotrope with water.

* * * * *